United States Patent [19]

Oleksyszyn et al.

[11] Patent Number: 5,216,022
[45] Date of Patent: Jun. 1, 1993

[54] AROMATIC ESTERS OF PHENYLENEDIALKANOATES AS INHIBITORS OF HUMAN NEUTROPHIL ELASTASE

[75] Inventors: Jozef Oleksyszyn, Westminster; Gary P. Kirschenheuter, Arvada, both of Colo.

[73] Assignee: Cortech, Inc., Denver, Colo.

[21] Appl. No.: 809,378

[22] Filed: Dec. 19, 1991

[51] Int. Cl.⁵ .................. A61K 31/215; C07C 69/773
[52] U.S. Cl. .................... 514/533; 514/534; 514/538; 560/8; 560/11; 560/12; 560/20
[58] Field of Search .......... 560/8, 11, 12, 20; 514/533, 534, 538

[56] References Cited

PUBLICATIONS

Chemical Abstract 109(7) #54438m, 1988 Kobyashi et al.

Primary Examiner—John M. Ford
Assistant Examiner—Y. N. Gupta
Attorney, Agent, or Firm—Cushman, Darby & Cushman

[57] ABSTRACT

Compounds of the formula

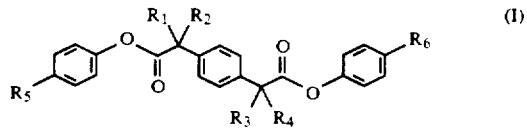

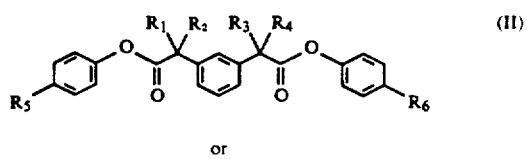

or

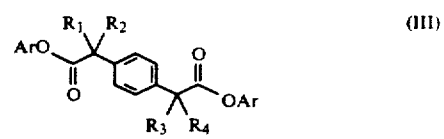

wherein:

$R_1$, $R_2$, $R_3$ and $R_4$, which may be the same or different, are selected from the group consisting of hydrogen, alkyl of 1–6 carbons, cycloalkyl of 3 to 6 carbons, alkenyl of 2–6 carbons, or together represent methylene groups —$(CH_2)_n$— where n is a whole number from 1 to 6, provided that $R_1$ and $R_2$ or $R_3$ and $R_4$ are not both hydrogen;

$R_5$ and $R_6$, which may be the same or different, are selected from the group consisting of hydrogen, halogen, nitro or —$S(O)_nR_7$ where n is 0, 1 or 2 and $R_7$ is an optionally substituted alkyl of 1–12 carbons atoms; and both Ar substituents are optionally substituted heteroaromatic rings or one Ar is such heteroaromatic ring and the other is optionally substituted phenyl, the optional substitution for Ar being halogen, nitro or —$S(O)_nR_7$ where n and $R_7$ have the value given above. The compounds are useful as inhibitors of human neutrophil elastase.

13 Claims, No Drawings

AROMATIC ESTERS OF PHENYLENEDIALKANOATES AS INHIBITORS OF HUMAN NEUTROPHIL ELASTASE

The present invention relates to certain phenylenedialkanoate esters which are useful as inhibitors of human neutrophil elastase (HNE) or equivalently human leukocyte elastase (HLE).

RELATED APPLICATIONS

This application is related to U.S. applications Ser. No. 07/528,967 filed May 22, 1990; Ser. No. 07/610,207 filed Nov. 7, 1990; and Ser. No. 07/692,322 filed May 2, 1991, the contents of which are incorporated herein by reference.

BACKGROUND OF THE INVENTION

HNE is a degradative enzyme implicated in a significant number of human disease states such as adult respiratory distress syndrome (ARDS), emphysema, inflammatory bowel disease, ischemia reperfusion injury (myocardial infarction), periodontal disease, dermatitis, psoriasis, cystic fibrosis, chronic bronchitis, artherosclerosis, alzheimers disease and arthritis. There is a need for effective inhibitors of HNE as therapeutic and as prophylactic agents for the treatment and/or prevention of elastase-mediated problems. Typical prior efforts to deal with elastase inhibition are disclosed in the patent literature, for instance U.S. Pat. Nos. 4,683,241 and 4,801,610.

SUMMARY OF THE INVENTION

The principal object of the present invention is to provide certain new compounds which are useful as human neutrophil elastase inhibitors. These compounds are characterized by their relatively low molecular weight, high potency and selectively with respect to HNE. They can be used effectively to prevent, alleviate or otherwise treat disease states characterized by the degradation of connective tissue by proteases in humans.

The novel compounds of the invention may be structurally illustrated by the following formulae (I-III):

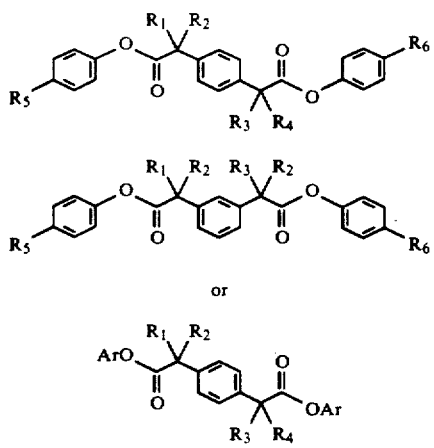

wherein:

$R_1$, $R_2$, $R_3$ and $R_4$, which may be the same or different, are selected from the group consisting of hydrogen, alkyl of 1–6 carbons, cycloalkyl of 3 to 6 carbons, alkenyl of 2–6 carbons, or together represent methylene groups $—(CH_2)_n—$ where n is a whole number from 1 to 6, provided that $R_1$ and $R_2$ or $R_3$ and $R_4$ are not both hydrogen;

$R_5$ and $R_6$, which may be the same or different, are selected from the group consisting of hydrogen, halogen (F, Cl, Br), nitro or $—S(O)_nR_7$ where n is 0, 1 or 2 and $R_7$ is an optionally substituted alkyl of 1–12 carbons including for example, lower alkyl (1–6 carbons) bearing a carboxylic acid group such as $—CH_2CO_2H$, $—C(CH_3)_2CO_2H$ or especially $—CH_2C(CH_3)_2CO_2H$ or the corresponding ester group, i.e. $—CH_2CO_2R_6$, $—C(CH_3)_2CO_2R_6$ or $—CH_2C(CH_3)_2CO_2R_6$ where $R_4$ is lower alkyl such as methyl, ethyl, propyl or butyl; and both Ar substituents are optionally substituted heteroaromatic rings or one Ar is an optionally substituted heteroaromatic ring and the other is optionally substituted phenyl, the optional substitution for Ar being halogen, nitro or $—S(O)_nR_7$ where n and $R_7$ have the values given above.

It will be appreciated that when $R_1$ and $R_2$ are different and/or $R_3$ and $R_4$ are different, the resulting compounds may exist as pairs of enantiomers. When $R_5$ or $R_6$ is $—S(O)R_7$ the resulting sulfoxides may exist as pairs of enantiomers as well. It will be appreciated further that a number of diastereomers are possible for compounds of the invention which contain more than one chiral center. The invention contemplates mixtures of these diastereomers as well as the individual components of these mixtures and the separate (+ and −) enantiomers in addition to the racemic mixtures (+/−) thereon.

As indicated by formula (III), it is contemplated that one or both of the $R_5$- and $R_6$-phenyl groups of the formula (I) and (II) esters may be replaced by an optionally substituted heteroaromatic ring (Ar) as depicted in formula (III). Such Ar substitutions may include pyridinyl or pyrimidinyl groups such as the 6-((2-methylmercapto)-1,3-pyrimidinyl) group or the corresponding pyridinyl group.

The two Ar substituents in the formula (III) compounds may be the same or different.

Representative alkyl values for $R_1$, $R_2$, $R_3$ and $R_4$ include, for example, methyl, ethyl, propyl n-butyl, isobutyl, t-butyl, pentyl or hexyl. Cycloalkyl includes, for example, cyclopropyl, cyclobutyl, cyclopentyl and cyclohexyl while representative alkenyl substituents are ethenyl, propenyl, butenyl and the like.

Non-toxic, pharmaceutically acceptable salts and esters of the indicated compounds are also contemplated. This includes, for example, alkali metal salts and lower alkyl esters.

PREFERRED EMBODIMENTS OF THE INVENTION

Particularly advantageous for present purposes are the compounds of formulas (I) and (II) wherein $R_1$, $R_2$, $R_3$ and $R_4$ are the same and are methyl groups, or where $R_1$ and $R_2$ taken together and $R_3$ and $R_4$ taken together represent methylene groups $—(CH_2)_n—$ where $n=3$.

It has been found that compounds wherein $R_5$ and $R_6$ are $—SCH_2C(CH_3)_2CO_2H$ are also particularly useful. These compounds can be oxidized in vivo by oxidants to give the more potent sulfoxides wherein $R_5$ and $R_6$ are $S(O)CH_2C(CH_3)_2CO_2H$ and ultimately the sulfones wherein $R_5$ and $R_6$ are $S(O)_2CH_2C(CH_3)_2CO_2H$. The potency of the compounds of the invention toward HNE increases in the series:

sulfide < sulfoxide < sulfone.

As a result, the inhibitors of HNE may be administered as the sulfide and converted to the more potent sulfoxides and/or sulfones by in vivo oxidants present at the site of HNE-mediated damage.

Representative examples of compounds according to the invention are given hereinafter in Tables I–III.

REACTION SCHEME A

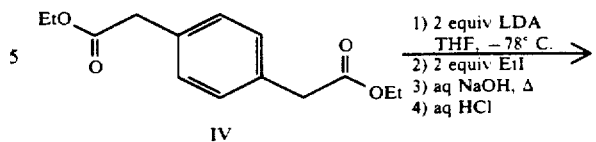

1) 2 equiv LDA THF, −78° C.
2) 2 equiv EtI
3) aq NaOH, Δ
4) aq HCl

TABLE I

This table exemplifies compounds of Formula (I) wherein $R_1$, $R_2$, $R_3$, $R_4$, $R_5$ and $R_6$ have the values indicated.

| CMPD # | | |
|---|---|---|
| 1 | $R_1 = R_3 = H \; R_2 = R_4 = C_2H_5$ | $R_5 = R_6 = SCH_3$ |
| 2 | $R_1 = R_3 = H \; R_2 = R_4 = C_2H_5$ | $R_5 = R_6 = S(O)CH_3$ |
| 3 | $R_1 = R_3 = H \; R_2 = R_4 = C_2H_5$ | $R_5 = R_6 = S(O)_2CH_3$ |
| 4 | $R_1 = R_3 = H \; R_2 = R_4 = C_2H_5$ | $R_5 = R_6 = SCH_2C(CH_3)_2CO_2H$ |
| 5 | $R_1 = R_3 = H \; R_2 = R_4 = C_2H_5$ | $R_5 = R_6 = S(O)CH_2C(CH_3)_2CO_2H$ |
| 6 | $R_1 = R_3 = H \; R_2 = R_4 = C_2H_5$ | $R_5 = R_6 = S(O)_2CH_2C(CH_3)_2CO_2H$ |
| 7 | $R_1 = R_3 = H \; R_2 = R_4 = C_2H_5$ | $R_5 = R_6 = SC(CH_3)_2CO_2H$ |
| 8 | $R_1 = R_3 = H \; R_2 = R_4 = C_2H_5$ | $R_5 = R_6 = S(O)C(CH_3)_2CO_2H$ |
| 9 | $R_1 = R_3 = H \; R_2 = R_4 = C_2H_5$ | $R_5 = R_6 = S(O)_2C(CH_3)_2CO_2H$ |
| 10 | $R_1 = R_2 = R_3 = R_4 = CH_3$ | $R_5 = R_6 = SCH_2C(CH_3)_2CO_2H$ |
| 11 | $R_1 = R_2 = R_3 = R_4 = CH_3$ | $R_5 = R_6 = S(O)CH_2C(CH_3)_2CO_2H$ |
| 12 | $R_1 = R_2 = R_3 = R_4 = CH_3$ | $R_5 = R_6 = S(O)_2CH_2C(CH_3)_2CO_2H$ |
| 13 | $R_1 = R_2 = R_3 = R_4 = CH_3$ | $R_5 = R_6 = SCH_2CO_2H$ |
| 14 | $R_1 = R_2 = R_3 = R_4 = CH_3$ | $R_5 = R_6 = S(O)CH_2CO_2H$ |
| 15 | $R_1 = R_2 = R_3 = R_4 = CH_3$ | $R_5 = R_6 = S(O)_2CH_2CO_2H$ |
| 16 | $R_1, R_2 = -(CH_2)_3- R_3, R_4 = -(CH_2)_3-$ | $R_5 = R_6 = SCH_2C(CH_3)_2CO_2H$ |
| 17 | $R_1, R_2 = -(CH_2)_3- R_3, R_4 = -(CH_2)_3-$ | $R_5 = R_6 = S(O)CH_2C(CH_3)_2CO_2H$ |
| 18 | $R_1, R_2 = -(CH_2)_3- R_3, R_4 = -(CH_2)_3-$ | $R_5 = R_6 = S(O)_2CH_2C(CH_3)_2CO_2H$ |

TABLE II

This table exemplifies compounds of Formula (II) wherein $R_1$, $R_2$, $R_3$, $R_4$, $R_5$ and $R_6$ have the values indicated.

| CMPD # | | |
|---|---|---|
| 19 | $R_1 = R_3 = H \; R_2 = R_4 = C_2H_5$ | $R_5 = R_6 = SCH_2C(CH_3)_2CO_2H$ |
| 20 | $R_1 = R_3 = H \; R_2 = R_4 = C_2H_5$ | $R_5 = R_6 = S(O)CH_2C(CH_3)_2CO_2H$ |
| 21 | $R_1 = R_3 = H \; R_2 = R_4 = C_2H_5$ | $R_5 = R_6 = S(O)_2CH_2C(CH_3)_2CO_2H$ |
| 22 | $R_1 = R_2 = R_3 = R_4 = CH_3$ | $R_5 = R_6 = SCH_2C(CH_3)_2CO_2H$ |
| 23 | $R_1 = R_2 = R_3 = R_4 = CH_3$ | $R_5 = R_6 = S(O)CH_2C(CH_3)_2CO_2H$ |
| 24 | $R_1 = R_2 = R_3 = R_4 = CH_3$ | $R_5 = R_6 = S(O)_2CH_2C(CH_3)_2CO_2H$ |
| 25 | $R_1, R_2 = -(CH_2)_3- R_3, R_4 = -(CH_2)_3-$ | $R_5 = R_6 = SCH_2C(CH_3)_2CO_2H$ |
| 26 | $R_1, R_2 = -(CH_2)_3- R_3, R_4 = -(CH_2)_3-$ | $R_5 = R_6 = S(O)CH_2C(CH_3)_2CO_2H$ |
| 27 | $R_1, R_2 = -(CH_2)_3- R_3, R_4 = -(CH_2)_3-$ | $R_5 = R_6 = S(O)_2CH_2C(CH_3)_2CO_2H$ |

TABLE III

This table exemplifies the compounds of formula (III) wherein $R_1$, $R_2$, $R_3$, $R_4$ and Ar have the values specified.

| CMPD # | | |
|---|---|---|
| 28 | $R_1 = R_3 = H$ $R_2 = R_4 = C_2H_5$ | Ar = 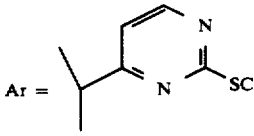 |

The products of the invention may be prepared by procedures available to those skilled in the art. A representative synthesis procedure may be illustrated by the following Reaction Schemes A–D:

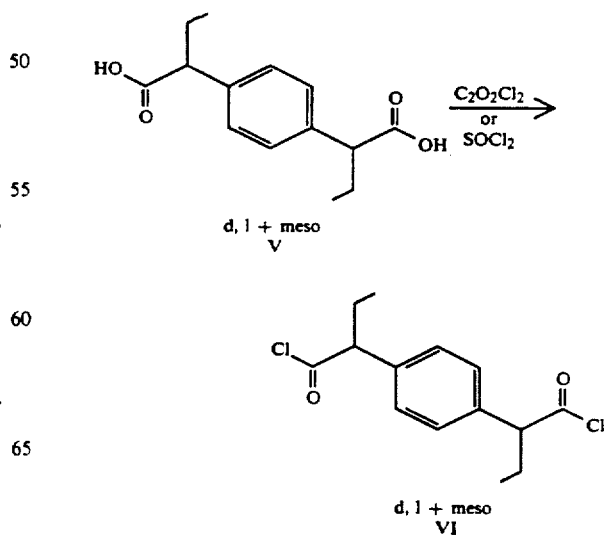

d, l + meso
V d, l + meso
VI

-continued
REACTION SCHEME A
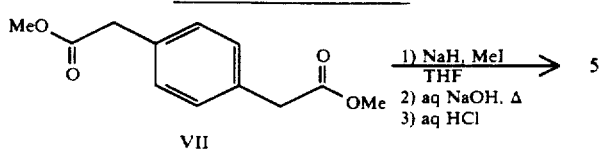
VII
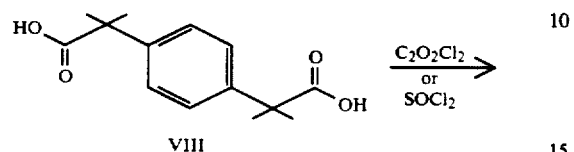
VIII
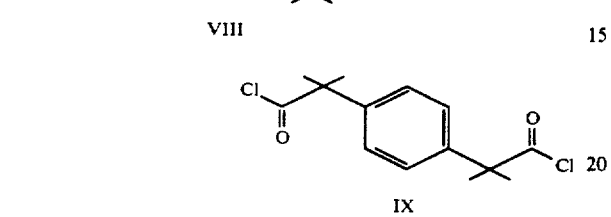
IX
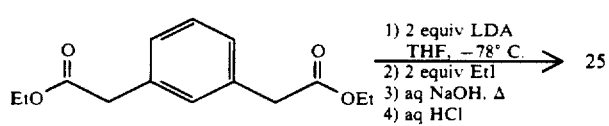
X
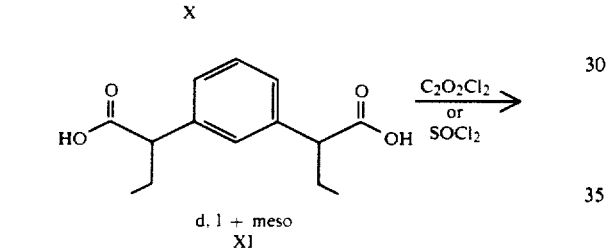
d, l + meso
XI
-continued
REACTION SCHEME A
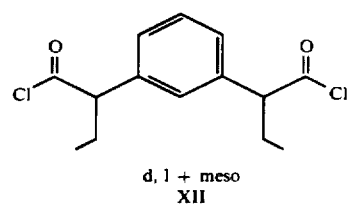
d, l + meso
XII
REACTION SCHEME B
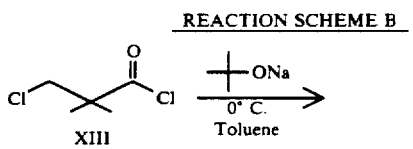
XIII
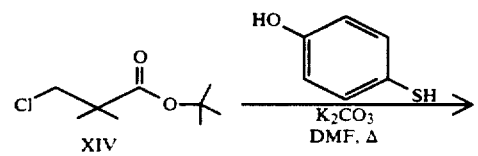
XIV
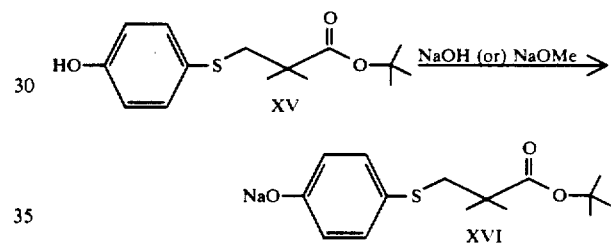
XV
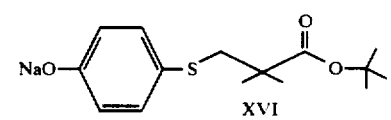
XVI
REACTION SCHEME C
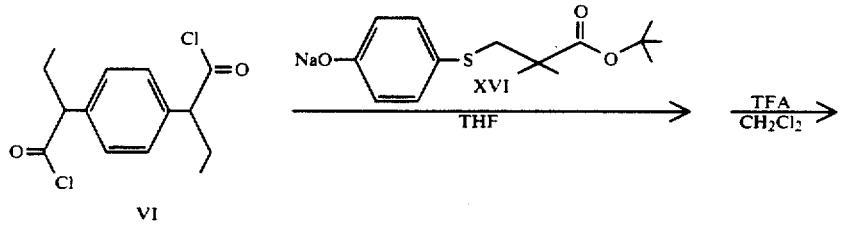
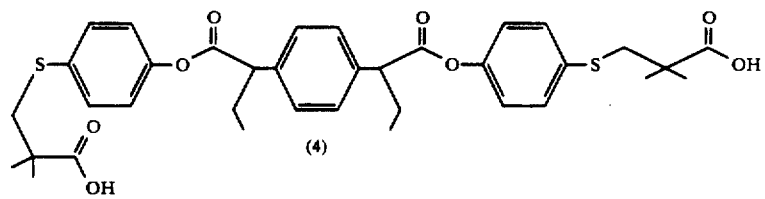
(4)
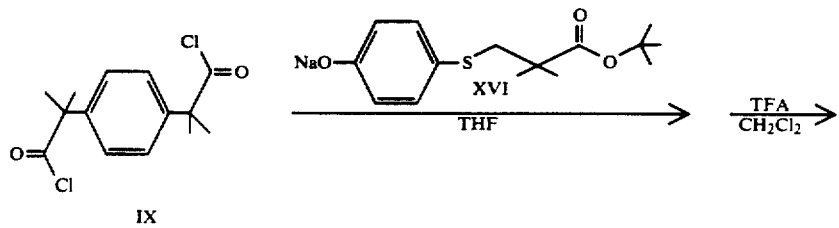

-continued
REACTION SCHEME C
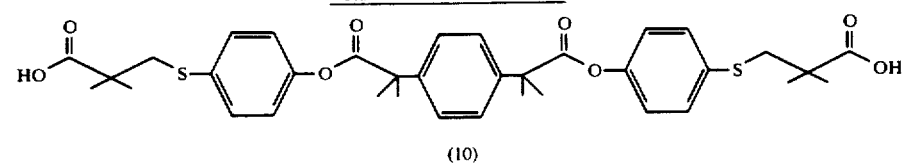
(10)
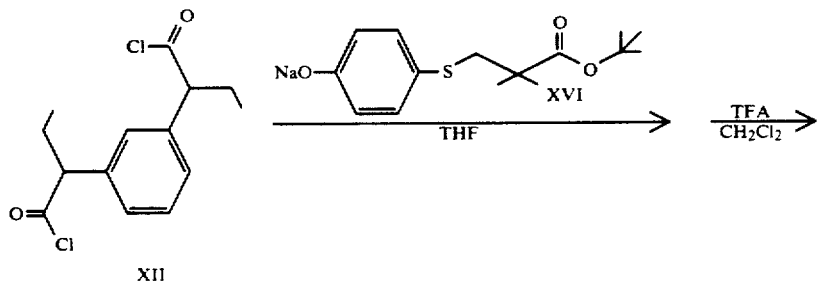
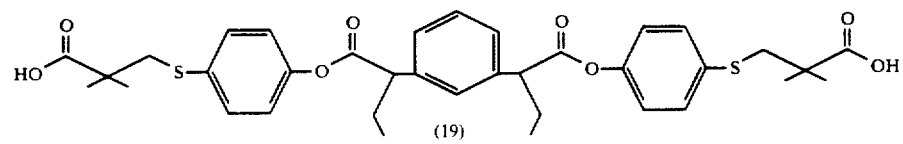
(19)
REACTION SCHEME D
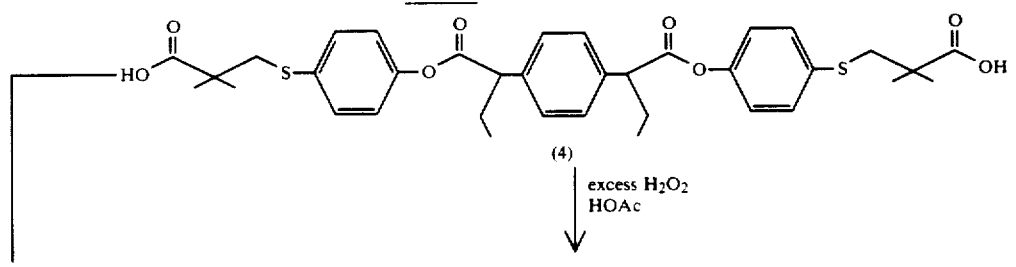
(4)
↓ excess H₂O₂
HOAc
(6)
2 equiv H₂O₂
HOAc →
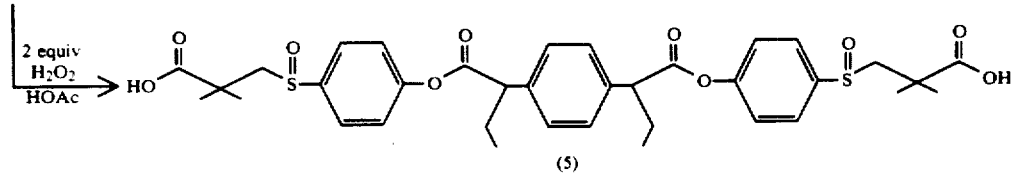
(5)
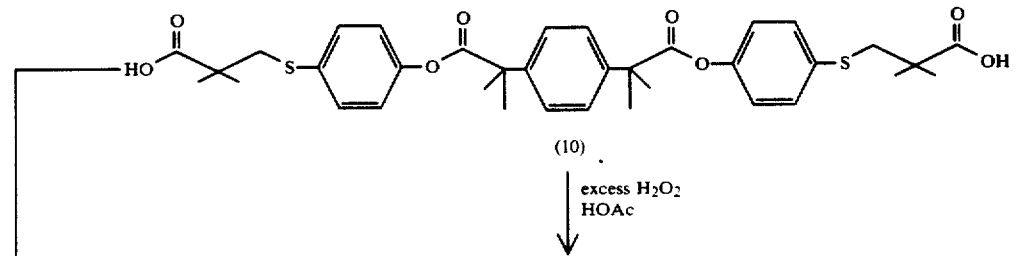
(10)
↓ excess H₂O₂
HOAc

-continued
REACTION SCHEME D

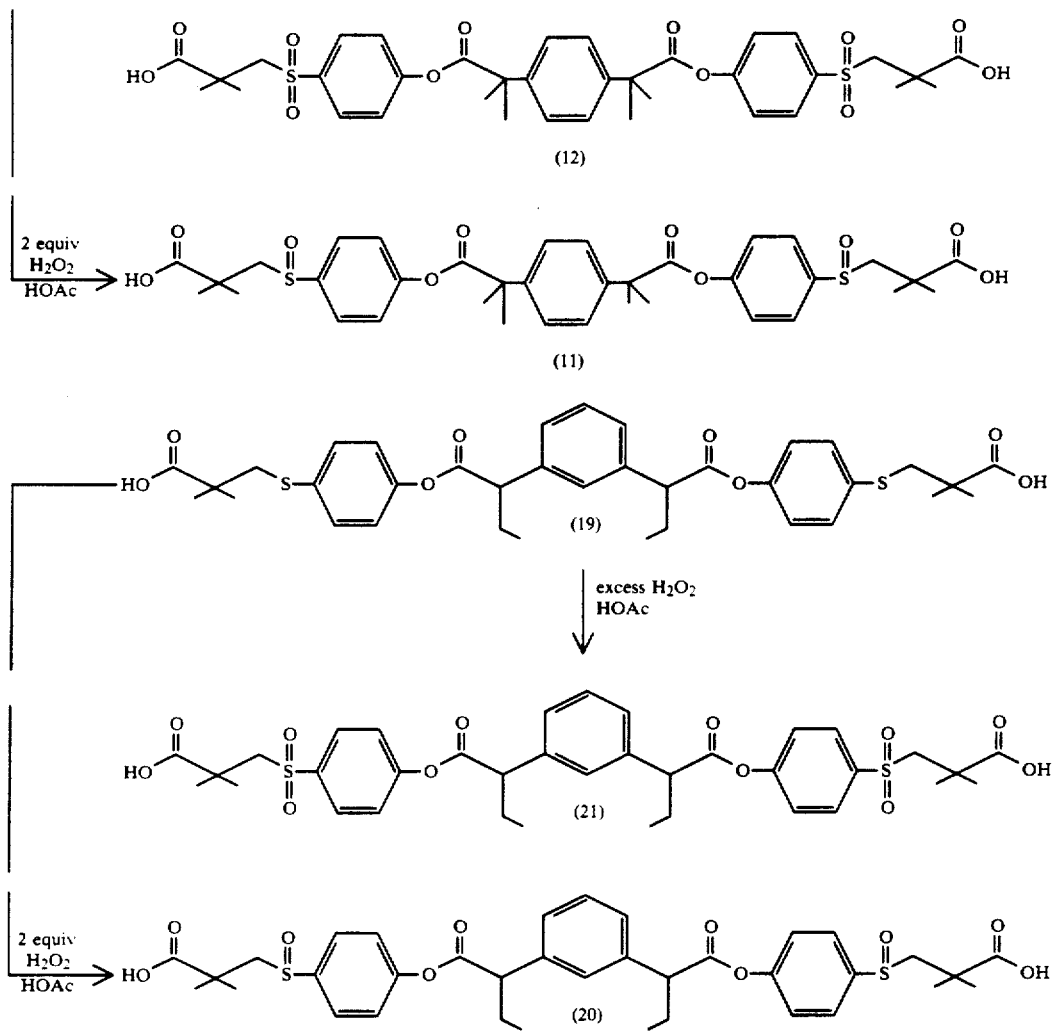

The commercially available 1,3-phenylenediacetic acid and the 1,4-phenylenediacetic acid may be esterified by standard methods to give the respective diesters (IV). The diethyl derivative (IV) may be alkylated by treatment with lithium diisopropylamine (LDA) followed by iodoethane and subsequently hydrolyzed to the diacid (V) which is a mixture of d,l and meso compounds. Treatment of (V) with either thionyl chloride or oxalyl chloride affords the diastereomeric mixture of dichlorides (VI). Similarly, the 1,3-diester (X) may be converted to the dibutyric acids (XI) and further to the dichlorides (XII). The dimethyl ester (VII) may be subjected to exhaustive methylation in the presence of sodium hydride and iodomethane followed by hydrolysis to afford the diacid (VIII). The dichloride (IX) may be obtained by allowing the diacid (VIII) to react with thionyl chloride or oxalyl chloride.

The synthesis of the phenol derivative (XV) is outlined in Scheme B. Commercially available 3-chloropivaloyl chloride and sodium tertbutoxide are allowed to react at 0° C. in toluene. Subsequent reaction of the chloro ester (XIV) with commercially available 4-hydroxythiophenol in the presence of potassium carbonate in DMF gives the phenol (XV) in high overall yield. If desired, the phenol (XV) can be converted to the sodium salt (XVI) by treatment with sodium hydroxide or sodium methoxide. The synthetic sequence of Scheme B is general and may be utilized for the synthesis of all the phenolic compounds needed for the synthesis of the compounds of the invention.

The dichlorides synthesized according to Scheme A and the phenolic compounds generated using Scheme B may be combined to yield the aromatic diesters of the invention as illustrated in Scheme C. The dichlorides (VI) react smoothly with the phenolate (XVI) in THF to give, after deprotection with trifluoroacetic acid (TFA), the aromatic diester (4). The same sequence may be used to synthesize any of the diesters such as (10) and (19). Alternatively, the dichlorides from Scheme A may be treated with the phenol (XV) in the presence of an organic base such as triethylamine. Subsequent deprotection with trifluoroacetic acid yields the desired aromatic diesters.

The sulfides such as compounds (4), (10) and (19) may be oxidized to the sulfoxides (5), (11) and (20) respectively by treatment with two equivalents of hydrogen peroxide, in acetic acid as illustrated in Scheme D. Further oxidation to the respective sulfones (6), (12) and

(21) may be accomplished in the presence of excess hydrogen peroxide in acetic acid for 1-2 days. These oxidation reactions are general and may be utilized in the synthesis of all of the sulfoxides and sulfones described in the invention.

It will be appreciated that there are additional methods of synthesizing the compounds of the invention which are available to one skilled in the art.

The following examples illustrate the preparation of specific compounds according to the invention.

EXAMPLE 1

Synthesis of Compound 1

A) 2,2'-(1,4-Phenylene)dibutyric acid (V)

Diethyl 1,4-phenylenediacetate (9.50 g, 0.033 mol) in 20 mL of dry THF was added to a solution of 50.6 mL of a 1.5M LDA solution (hexanes) in 200 mL of THF at $-78°$ C. under nitrogen. The resulting orange solution was stirred at $-78°$ C. for 1 hour and iodoethane (6.08 ml, 0.076 mol) was added in one portion via syringe. After stirring for an additional 2 hours at $-78°$ C., the reaction was allowed to warm to room temperature and proceed overnight. The reaction mixture was quenched with water and the layers separated. The organic phase was washed with 10% citric acid, water, and then concentrated to give the crude diester as an oil. The diester was hydrolyed by heating in a solution of NaOH (3.6 g, 0.09 mol) in 20 mL of $H_2O$ and 20 mL of ethanol. After four hours the volatiles were removed under vacuum and the residue acidified to pH 1 with concentrated hydrochloric acid. The precipitated solid was filtered, air-dried and recrystallized from THF/hexane to give 4.0 g (42%) of the desired diacid. mp 198°-202° C.; $^1$H NMR (CDCl$_3$) $\delta$0.83-1.0 (m,6H), 1.53-1.83 (m,2H), 1.93-2.18 (m,2H), 3.33-3.46 (m,2H), 7.13-7.43 (ArH,4H).

B) Bis(4-Methylmercaptophenyl)2'-(1,4-phenylene)-dibutyrate(1)

Excess oxalyl chloride was added to 2,2'-(1,4-phenylene)dibutyric acid (876 mg, 3.5 mmol) in $CH_2Cl_2$. Upon completion of the reaction the volatiles were removed and the dichloride (VI) was added to 4-methylmercaptophenol (1.32 g, 9.4 mmol) and 1.4 mL of triethylamine in THF. The reaction was followed by TLC until complete. Toluene was added and the mixture washed successively with water, 5% sodium hydroxide, water, 10% citric acid, and water. After drying over MgSO$_4$ the solution was concentrated and the residue recrystallized from $CH_2Cl_2$/hexane to afford the product as a white solid. mp 45°-48° C.; $^1$H NMR (CDCl$_3$) $\delta$1.00 (t,6H,J=7.4 Hz), 1.81-1.98 (m,2H), 2.15-2.32 (m,2H), 2.45 (s,6H), 3.70 (t,2H,J=7.4 HZ), 6.94 (d,4H,J=8.4 Hz), 7.23 (d,4H,J=8.7 Hz), 7.39 (s,4H); $^{13}$C NMR (CDCl$_3$) $\delta$ 11.91, 16.23, 26.55, 52.96, 122.0, 128.1, 128.5, 135.8, 137.9, 148.7, 172.9; IR (NaCl, film) 2365, 2922, 2875, 1754, 1750, 1489, 1202, 1167, 1140, 1088, 1014 cm$^{-1}$.

EXAMPLE 2

Synthesis of Intermediate XV

A) Synthesis of tert-Butyl 3-chloro-pivaloate (XIV)

A slurry of sodium tert-butoxide (195.3 g, 2.03 mol) in 800 mL of dry toluene was cooled to 0° C. in an ice bath. To the stirred slurry was added 3-chloropivaloyl chloride (XIII) (300.0 g 1.94 mol) dropwise at a rate sufficient to maintain the reaction temperature below 10° C. After the addition was complete, the reaction mixture was allowed to warm to room temperature and stirred overnight. The reaction was quenched with water, the mixture extracted with ether, and the ether layer washed with water and saturated NaHCO$_3$. After drying over MgSO$_4$, the solution was filtered and concentrated to give the product as an amber oil. $^1$H NMR (CDCl$_3$) $\delta$ 1.24 (s,6H), 1.46 (s,9H), 3.57 (s,2H); $^{13}$C NMR (CDCl$_3$) $\delta$ 22.96, 27.70, 44.80, 53.32, 80.87, 174.5.

B) Synthesis of tert-Butyl 3-(4'-Hydroxyphenyl)mercaptopivaloate (XV)

To a slurry of 4-hydroxythiophenol (259.4 g, 2.06 mol) and potassium carbonate (284.2 g, 2.06 mol) in 500 mL of DMF at 0° C. was added tert-butyl 3-chloropivaloate (373.8 g, 1.94 mol) dropwise over 2 hours. After stirring to room temperature overnight, the reaction was heated to 110° C. for 3 hours. The reaction was allowed to cool for room temperature and water and ether were added. The layers were separated and the organic layer washed with water and 5% NaOH, dried over MgSO$_4$ and concentrated. The resulting oil was recrystallized from 1:3 $CH_2Cl_2$/pet. ether to afford 328.0 g (60%) of the desired product. mp 100°-100.5° C.; $^1$H NMR (CDCl$_3$) $\delta$1.22 (s,6H), 1.44 (s,9H), 3.07 (s,2H), 5.42 (br s,1H,—OH), 6.77 (d,2H,J=8.7 Hz); $^{13}$C NMR (CDCl$_3$) $\delta$ 24.62, 27.73, 44.58, 46.86, 81.00, 116.2, 127.7, 133.5, 155.4, 176.7; IR (KBr, film) 3362, 2971, 1720, 1693, 1600, 1583, 1495, 1472, 1366, 1320, 1223, 1150(s), 835, 817 cm$^{-1}$.

EXAMPLE 3

Synthesis of Compound 10

A) Synthesis of Dimethyl 2,2'-(1,4-Phenylene)diisobutyrate

A solution of dimethyl 2,2'-(1,4-phenylene)diacetate (79.0 g, 0.35 mol) and iodomethane (252 g, 1.78 mol) in 300 ml of dry THF was added to a slurry of sodium hydride (42.6 g, 1.78 mol) in 500 mL of THF dropwise over 30 minutes. After completion of the addition, the reaction mixture was heated under reflux for 2 hours. The reaction was allowed to cool to room temperature, filtered through Celite and concentrated. The residue was dissolved in Et$_2$O, washed with H$_2$O, and drived over MgSO$_4$. Evaporation of the solvent afforded 90.0 g (91%) of the desired product. $^1$H NMR (CDCl$_3$), $\delta$1.56 (s,12H), 3.65 (s,6H), 7.27 (s,4H).

B) Synthesis of 2,2'-(1,4-Phenylene)diisobutyric Acid (VIII)

A mixture of dimethyl 2,2'-(1,4phenylene)diisobutyrate and 1:1 EtOH/5N NaOH (1.1 equiv) were heated to reflux for 4 hours. The EtOH was distilled in vacuo, the residual solution acidified to pH2 with concentrated HCl and the precipitated solid filtered. The white solid (70% yield) was air-dried and suitable for use without further purification. mp 268°-270° C.; $^1$H NMR (DMSO-d$_6$) $\delta$ 1.56 (s,12H), 7.50 (s,4H), 12.3 (br s,2H, —CO$_2$H); IR (KBr) 1687 cm$^{-1}$.

C) Synthesis of 2,2'-(1,4-Phenylene)diisobutyryl Dichloride (IX)

A mixture of 2,2'-(1,4-phenylene)diisobutyric acid (121 g, 0.48 mol) and thionyl chloride (144 g, 1.21 mol) in 500 mL of toluene was heated under reflux for 16 hours. The volatiles were removed under vacuum and the residue distilled (bp ~130° C., 0.6 mm Hg) to afford 94 g (68%) of the product as a solid. mp 114°-116° C.; IR (KBr) 1787 cm$^{-1}$ (—C(O)Cl—).

D) Synthesis of Bis(4-(2'-Carbo-tert-butoxy-2'-methylpropylmercapto)-phenyl) 2,2'-(1,4-Phenylene)diisobutyrate A solution of sodium methoxide (31.6 g, 0.58 mol) was added to tert-butyl 3-(4'-hydroxyphenol)mercaptopivaloate (XV) (165.2 g, 0.58 mol) in 200 mL of methanol and the resulting solution was stirred for 1 hour. The solution was concentrated under vacuum and the residual methanol was removed by azeotropic distillation with toluene. The crude sodium salt was dried under vacuum for 16 hours and used without further purification. The dried sodium salt was dissolved 800 mL of dry THF, 40 mL of triethylamine was added and a solution of 2,2'-(1,4-phenylene)diisobutyryl dichloride (IX) (94 g 0.33 mol) in 200 mL of THF was added dropwise. After the addition was completed, the reaction mixture was stirred for 16 hours at room temperature. The reaction was quenched with 1 L of H$_2$O and ether was added. The organic layer was separated and washed with water, dilute NaHCO$_3$ and passed through a pad of silica gel. The solution was evaporated and the residue recrystallized from hexane to afford 142 g (56%) of the product as a white solid. $^1$H NMR (CDCl$_3$) δ 1.22 (s,12H), 1.43 (s,18H), 1.71 (s,12H), 3.10 (s,4H), 6.89 (d,J=8.6 Hz, 4H), 7.40 (d,J=8.6 Hz, 4H), 7.44 (s,4H).

E) Synthesis of Bis(4-(2'-Carboxy-2'-methylpropylmercapto)phenyl 2,2'-(1,4-Phenylene)diisobutyrate (10)

Trifluoroacetic acid (50 mL) was added to a stirred solution of bis-(4-(2'-carbo-tert-butoxy-2'-methylpropylmercapto)phenyl) 2,2'-(1,4-phenylene)diisobutyrate (142 g, 182 mmol) in 1 L of methylene chloride. After 16 hours an additional 50 mL of trifluoroacetic acid was added and the reaction was allowed to continue for another 16 hours. Methylene chloride (500 mL) and H$_2$O (1 L) were added and the layers were separated. The organic phase was washed with H$_2$O, 1 L of hexane was added and the resulting solution placed in the freezer for 6 hours. The solid was filtered and dried in the vacuum oven for 16 hours to give 100 g (81%) of the desired product. mp 173°-174° C.; $^1$H NMR (CDCl$_3$) 1.26 (s,12H), 1.71 (s,12H), 3.15 (s,4H), 6.88 (d,J=8.7 Hz, 4H), 7.35 (d,J=8.7 Hz,4H), 7.44 (s,4H).

EXAMPLE 4

General Procedure for Preparation of Bis(sulfoxides) 2, 5, 8, 11, 14, 17, 20, 23 and 26

A sample of the bis(sulfide) diester derivative (~0.3 g) was dissolved in acetic acid and 30% hydrogen peroxide (2 equiv) was added. The reaction was monitored by TLC and was judged complete when all of the starting material had been consumed (2-3 hours). The solvent was evaporated and the product was dried under vacuum.

EXAMPLE 5

General Procedure for the Preparation of Bis(sulfones) 3, 6, 9, 12, 15, 18, 21, 24 and 27

A sample of the bis(sulfide) diester derivative (1, 4, 7, 10, 13, 16, 19, 22 or 25) was dissolved in acetic acid (heating may be required) and 30% hydrogen peroxide (10 equiv H$_2$O$_2$/1 mol diester) was added. The reaction mixture was stirred for 24-48 hours and the solvents were removed under vacuum. The product may be purified by chromatography or recrystallization as deemed necessary.

| Compound 3: | mp 164-166° C. (THF/hexane); $^1$H NMR (CDCl$_3$)δ1.01(t, 6H), 2.23-1.95 (m, 4H), 3.75(t, 2H)7.24 (d, J=9 Hz, 4H), 7.41(s, 4H)7.96(d, J=9Hz, 4H); IR(KBr, film)2967, 2930, 2877, 1754, 1589, 1487, 1460, 1409, 1314, 1293, 1205 cm$^{-1}$. |
|---|---|

EXAMPLE 6

Synthesis of Bis(4-(2'-Carboxy-2'-methylpropylsulfonyl)phenyl) 2,2'-(1,4-Phenylene)diisobutyrate(12)

To a 1-L three-neck flask fitted with a thermometer was added 15.00 g (0.0225 mol) of bis(4-(2'-carboxy-2'-methylpropylmercapto)phenyl)2,2'-(1,4-phenylene)-diisobutyrate (10)) and 375 mL of glacial acetic acid. This suspension was heated to 90° C. to give a homogeneous solution and 20.4 mL of hydrogen peroxide (30%) was added over a 2-3 minute period. The course of the reaction was followed by $^1$H NMR by observing the disappearance of the —SCH$_2$ signal (3.16 ppm) and the ultimate appearance of the —SO$_2$CH$_2$ signal (3.63 ppm) characteristic of the desired product. Compound 11, i.e. the sulfoxide (—SOCH$_2$) derivative, was formed as an intermediate in the course of the reaction and could have been separated as such. However, in this case, the sulfoxide was not isolated or characterized independently. Upon completion of the reaction, the resulting clear, colorless solution was allowed to cool at 25° C. The product precipitated as a white, flocculent solid which was filtered, washed with water and dried under vacuum at 50° C. in the presence of NaOH for 48 h to yield 14.65 g (89%) of the desired product (12). mp 162°-164° C.; $^1$H NMR (DMSO-d$_6$) 1.23 (s, 12 H), 1.68 (s, 12 H), 3.63 (s, 4H), 7.37 (d, J=8.7 Hz. 4H), 7.92 (d, J=8.7 Hz, 4H), 7.92 (d, J=8.7 Hz, 4 H), 12.46-12.64 (br s, 2H); $^{13}$C NMR (DMSO-d$_6$) δ24.84, 24.91, 26.18, 40.51, 46.38, 63.11, 122.6, 125.9, 129.2, 138.6, 142.3, 154.3, 174.2, 176.1.

As noted earlier, the present compounds inhibit HLE activity which indicates that these compounds would be useful in the treatment of such diseases as emphysema, arthritis, artheriosclerosis or the like. For such uses, the compounds would be administered by the usual routes, e.g., orally, intravenously, subcutaneously, interperitoneally or intramuscularly. For emphysema, the compounds would be administered in therapeutically effective amounts, usually orally or rectally, or as a mist for bronchial inhalation.

The efficacy of the compounds for the treatment of various diseases can be determined by scientific methods which are known in the art. The following are noted as examples in this regard:

| (a) | For acute respiratory distress syndrome, the method according to Human neutropil elastase (HNE) model - AARD, 1990; 141: 227-677, and Endotoxin induced acute lung injury model in mini-pigs - ARRD, 1990; 142:782-788 |
|---|---|

| (b) | is used; In ischemia/reperfusion, the method according to canine model of reperfusion injury, J. Clin. Invest., 1988; 81:624–629 may be used. |
|---|---|

The amount of the compound used to inhibit HLE will vary with the nature and extent of the condition involved. It is contemplated, for example, that mists containing from 0.05 to 20% of the active compound with dosages in the order of 2–100 mg per dosage unit several times a day would provide a therapeutically effective amount for the treatment of emphysema. On the other hand, for intravenous administration, there may be used 1–200 mg/kg body weight several times a day or as a continuous iv infusion. Variations and adjustments in the size of administration can be determined to provide the desired HLE inhibition.

Pharmaceutical compositions containing the active compounds of the invention may comprise tablets, capsules, solutions or suspensions with conventional nontoxic pharmaceutical carriers. These compositions may include the usual types of additives, e.g., disintegrating or suspending agents or the like. Compounds selected for intravenous use should be soluble in aqueous solutions, while those used in, for example, oral formulations need not be soluble. Topical formulations are also contemplated for use in treatment of, for example, dermatitis and acne.

The compounds of the invention are extremely potent and highly selective inhibitors of neutrophil elastase. The compounds also appear to show adequate serum stability. The water solubility of the compounds varies and it will be appreciated that the ultimate mode of administration for each compound will depend, at least to some extent, on the solubility of the compound involved.

Without intending to be limited to any theory of operation or function, it appears that the compounds of the invention bind to thee active site of neutrophil elastase. More particularly, it appears that the acyl group binds to the S substrate position; i.e., the valine or pro-valine region of the binding pocket and the leaving group extends into the S' positions.

Representative compounds of the invention have been compared according to their potency represented by the $IC_{50}$'s for human neutrophil elastase (HNE). The following results were obtained (TABLE IV).

TABLE IV

| CMPD # | $IC_{50}$ (μM) |
|---|---|
| 1 | 8.44 |
| 2 | 0.224 |
| 3 | 0.062 |
| 4 | 0.120 |
| 5 | 0.040 |
| 6 | 0.028 |
| 8 | 0.074 |
| 9 | 0.037 |
| 10 | 0.253 |
| 11 | 0.023 |
| 12 | 0.018 |
| 13 | 0.835 |
| 15 | 0.077 |
| 19 | 0.198 |
| 21 | 0.036 |
| 28 | 0.064 |

The following test has been used to determine the activity of the compounds of the present invention as set out in Table IV: Potency ($IC_{50}$ Determination)

Reagents

A) 0.075M sodium phosphate, 20% dimethyl sulfoxide (DMSO), pH 7.7 = substrate and inhibitor buffer B) 0.075M sodium phosphate no DMSO, pH 7.7 = inhibitor buffer C) 10 mM human neutrophil elastase (HNE) substrate = N-methoxysuccinyl-ala-ala-pro-val-pNA in DMSO D) 0.01 sodium acetate, pH 5.5 = enzyme buffer (storage)

E) HNE (1 mg) dissolved in 1 mL of reagent E for storage at −20° C.

Procedure

Make a 10 mM stock of the inhibitor in DMSO. Dilute an aliquot (10 μL) up to 1.0 mL in reagent A (100 μM). Serially dilute 100 μL of the 100 μM in reagent A. Apply 100 μL of the diluted material to the wells of a 96-well plate. Dilute an aliquot of reagent F 1:150 in reagent D, apply 50 μL aliquots to the indicator wells and incubate 7 minutes at room temperature.

The HNE substrate solution is made by taking 100 μl of reagent C into 500 μL of reagent A and 400 μL of reagent B. After the 7 minutes of incubation, the substrate (50 μL) is applied to each well. The HNE catalyzed reaction is then monitored spectrophotometrically at 405 nm using an ELISA plate reader machine (UVMAX, Molecular Devices) which processes the raw data with an on-board kinetics program. The enzyme activity is plotted against different inhibitor concentrations and $IC_{50}$ value is determined by using a curve fitting software program. Once the "screening" $IC_{50}$ has been approximated, a more precise $IC_{50}$ value can be obtained by examination of inhibitor concentrations around this value.

It will be appreciated that various modifications may be made in the invention described herein without departing from the spirit and scope of the invention as defined in the following claims wherein:

What is claimed is:

1. A compound of the formula

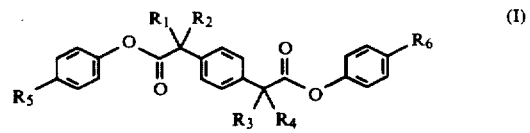

(I)

or

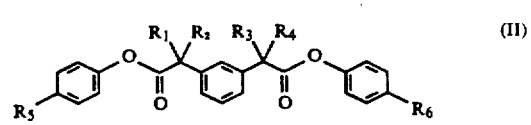

(II)

wherein:

$R_1$, $R_2$, $R_3$ and $R_4$, which may be the same or different, are selected from the group consisting of hydrogen, alkyl of 1–6 carbons, cycloalkyl of 3 to 6 carbons, alkenyl of 2–6 carbons, or together represent methylene groups —$(CH_2)_n$— where n is a whole number from 1 to 6, provided that $R_1$ and $R_2$ are not both hydrogen, and $R_3$ and $R_4$ are also not both hydrogen;

$R_5$ and $R_6$, which may be the same or different, are selected from the group consisting of halogen, nitro or —$S(O)_nR_7$ where n is 0, 1 or 2 and $R_7$ is an alkyl of 1-12 carbons atoms.

2. A compound according to claim 1 wherein $R_7$ is lower alkyl bearing a carboxylic acid or ester group.

3. A compound according to claim 2 wherein $R_7$ is —$CH_2CO_2H$, —$C(CH_3)_2CO_2H$ or —$CH_2C(CH_3)_2CO_2H$ or the lower alkyl esters thereof.

4. A compound according to claim 1 wherein $R_1$, $R_2$. $R_3$ and $R_4$ are each methyl.

5. A compound according to claim 1 wherein $R_1$ and $R_2$, together represent —$(CH_2)_n$—and $R_3$ and $R_4$ together represent —$(CH_2)_n$—wherein n is 3.

6. A compound according to any one of claims 1-5 wherein $R_5$ and $R_6$ are both —$SCH_2C(CH_3)_2CO_2H$.

7. A compound according to claim 1 wherein $R_1$, $R_2$, $R_3$ and $R_4$ are methyl and $R_5$ and $R_6$ are both —$SCH_2C(CH_3)_2CO_2H$.

8. A compound according to claim 1 wherein $R_1$, $R_2$, $R_3$ and $R_4$ are each methyl and $R_5$ and $R_6$ are both —$S(O)CH_2C(CH_3)CO_2H$.

9. A compound according to claim 1 wherein $R_1$, $R_2$, $R_3$ and $R_4$ are each methyl and $R_5$ and $R_6$ are both —$S(O)_2CH_2C(CH_3)_2CO_2H$.

10. A pharmaceutical composition comprising a compound according to claim 1 and a pharmaceutically acceptable carrier therfor.

11. A method of inhibiting human neutrophil elastase which comprises administering to a human in need of such inhibition, an effective amount of a compound according to claim 1.

12. A method of treating acute respiratory disease which comprises administering to a host in need of such treatment, an effective amount of a compound according to claim 1.

13. A method of treating ischemia/reperfusion which comprises administering to a host in need of such treatment, an effective amount of a compound according to claim 1.

* * * * *

UNITED STATES PATENT AND TRADEMARK OFFICE
CERTIFICATE OF CORRECTION

PATENT NO. : 5,216,022

DATED : June 1, 1993

INVENTOR(S) : OLEKSYSZYN et al.

It is certified that error appears in the above-identified patent and that said Letters Patent is hereby corrected as shown below:

In claim 8, column 18, lines 2 and 3, change "-S(O)CH$_2$C(CH$_3$)CO$_2$H" to -- -S(O)CH$_2$C(CH$_3$)$_2$CO$_2$H- --.

Signed and Sealed this

Tenth Day of December, 1996

Attest:

Attesting Officer

BRUCE LEHMAN

Commissioner of Patents and Trademarks